(12) United States Patent
Hsia

(10) Patent No.: US 11,896,624 B2
(45) Date of Patent: *Feb. 13, 2024

(54) COMPOSITIONS FOR ENHANCING HYPERTHERMIA THERAPY

(71) Applicant: Houn Simon Hsia, Tustin, CA (US)

(72) Inventor: Houn Simon Hsia, Tustin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/874,540

(22) Filed: Jul. 27, 2022

(65) Prior Publication Data

US 2022/0354903 A1 Nov. 10, 2022

Related U.S. Application Data

(63) Continuation of application No. 17/163,419, filed on Jan. 30, 2021, now Pat. No. 11,433,105, which is a continuation of application No. 16/007,524, filed on Jun. 13, 2018, now Pat. No. 10,905,724.

(60) Provisional application No. 62/519,090, filed on Jun. 13, 2017.

(51) Int. Cl.
| | | |
|---|---|---|
| A61K 36/00 | (2006.01) | |
| A61K 33/04 | (2006.01) | |
| A61P 35/00 | (2006.01) | |
| A61K 35/60 | (2006.01) | |

(52) U.S. Cl.
CPC .............. *A61K 35/60* (2013.01); *A61K 33/04* (2013.01); *A61P 35/00* (2018.01)

(58) Field of Classification Search
None
See application file for complete search history.

(56) References Cited

U.S. PATENT DOCUMENTS

| | | |
|---|---|---|
| 4,348,483 A | 9/1982 | Skogerson |
| 4,569,836 A | 2/1986 | Gordon |
| 5,810,888 A | 9/1998 | Fenn |
| 5,976,548 A | 11/1999 | Hsia |
| 6,077,828 A | 6/2000 | Abbruzzese |
| 6,197,295 B1 | 3/2001 | Hsia |
| 6,440,464 B1 | 8/2002 | Hsia |
| 6,576,233 B2 | 6/2003 | Hsia |
| 7,906,554 B2 | 3/2011 | Kelly |
| 8,017,147 B2 | 9/2011 | Mazed |
| 8,257,694 B2 | 9/2012 | Daikeler |
| 8,343,843 B2 | 1/2013 | Lee |
| 9,072,768 B2 | 7/2015 | Ranganathan |
| 9,095,602 B2 | 8/2015 | Gleave |
| 9,889,092 B2 | 2/2018 | Corbin |
| 10,206,861 B2 | 2/2019 | Seiberg |
| 10,905,723 B2 | 2/2021 | Hsia |
| 10,905,725 B2 | 2/2021 | Hsia |
| 2004/0072775 A1 | 4/2004 | Sobol |
| 2004/0087490 A1 | 5/2004 | Troup |
| 2005/0013875 A1 | 1/2005 | Kobayashi |
| 2006/0034944 A1 | 2/2006 | Ruslow |
| 2006/0088574 A1 | 4/2006 | Manning |
| 2006/0275506 A1 | 12/2006 | Fisher |
| 2007/0116802 A1 | 5/2007 | Germano |
| 2009/0110674 A1 | 4/2009 | Loizou |
| 2011/0008457 A1 | 1/2011 | Newman |
| 2011/0165255 A1 | 7/2011 | Kobayashi |
| 2011/0189220 A1 | 8/2011 | Yang |
| 2011/0195093 A1 | 8/2011 | Gunn |
| 2011/0229447 A1 | 9/2011 | Schiffrin |
| 2012/0010688 A1 | 1/2012 | Lamb |
| 2013/0008457 A1 | 1/2013 | Zheng |
| 2014/0294795 A1 | 10/2014 | Hsia |
| 2015/0004130 A1 | 1/2015 | Faber |
| 2015/0164964 A1 | 6/2015 | El-Nezamy |
| 2016/0067202 A1 | 3/2016 | Mathisen |
| 2016/0354344 A1 | 12/2016 | Robertson |
| 2017/0246136 A1 | 8/2017 | Diaz |
| 2018/0037263 A1 | 2/2018 | Kanasugi |
| 2018/0353550 A1 | 12/2018 | Hsia |
| 2021/0154241 A1 | 5/2021 | Hsia |

FOREIGN PATENT DOCUMENTS

| | | | |
|---|---|---|---|
| CA | 2010511 A1 * | 1/1990 | |
| CA | 105768108 A | 7/2016 | |
| CN | 104082736 A * | 10/2014 | ............... A23L 1/29 |
| CN | 105617358 | 6/2016 | |
| CN | 105641000 | 6/2016 | |
| CN | 105641000 A * | 6/2016 | |
| CN | 106822560 | 6/2017 | |
| DE | 2020013002760 U1 | 7/2014 | |
| JP | 06340544 | 6/1996 | |
| JP | 20121479 | 1/2012 | |

(Continued)

OTHER PUBLICATIONS

Extended European Search Report dated May 28, 2021, from related application 18817547.5. 17 pages.
Wang, Hang, et al. "Reduction of splenic immunosuppressive cells and enhancement of anti-tumor immunity by synergy of fish oil and selenium yeast," PLoS One 8(1):e52912. 10 pages.
Hwang, Jin-Taek, et al. Selenium Regulates Cyclooxygenase-2 and Extracellular Signal-Regulated Kinase Signaling Pathways by Activating AMPActivated Protein Kinase in Colon Cancer Cells. www.aacrjournals.org. Cancer Res 2006; 66: (20).Oct. 15, 2006. 7 pages.
Douwes, Friedrich. "Integrative Cancer Therapy Concept at St. George Hospital Germany," Klinik St. Georg. 6 pages.
Benswell Corporation Ltd, Prowell Nutritions "Good Health-Good Life" by Nutrawell, 2015, 18 pages, Retrieved from the Internet [URL: http://www.prowellnutritions.com].

(Continued)

*Primary Examiner* — Aaron J Kosar
*Assistant Examiner* — Randall O Winston
(74) *Attorney, Agent, or Firm* — Fish IP Law, LLP

(57) ABSTRACT

A composition for decreasing proliferation of cancer cells undergoing hyperthermia therapy is described. Such compositions can include a combination of selenium and fish oil. The respective quantities of selenium and fish oil are provided in amounts effective to synergistically increase the sensitivity of the cancer cells to temperatures in excess of 37° C.

3 Claims, 5 Drawing Sheets

(56) References Cited

FOREIGN PATENT DOCUMENTS

| | | | |
|---|---|---|---|
| JP | 2019529578 | 11/2020 | |
| WO | 0007607 | 2/2000 | |
| WO | 02076548 | 10/2002 | |
| WO | WO-02076548 A2 * | 10/2002 | ............... A61N 7/00 |
| WO | 2007079276 | 7/2007 | |
| WO | 2009091597 | 7/2009 | |
| WO | 2011115062 A1 | 9/2011 | |
| WO | 2012018597 | 2/2012 | |
| WO | 2012078745 | 6/2012 | |
| WO | 2012122295 | 9/2012 | |
| WO | 2014054884 | 4/2014 | |
| WO | 2015013932 | 2/2015 | |
| WO | 2018231937 | 12/2018 | |
| WO | 2018231938 | 12/2018 | |
| WO | 2018231943 | 12/2018 | |

OTHER PUBLICATIONS

Bren, Liiu, Nutritional Medicine and Cancer, Department of Otolaryngology, Taichung Chengchen General Hospital 2014, vol. 57, No. 5.
Choy and Milas, Journal of the National Cancer Institute (2003), vol. 95 (19), pp. 1140-1452.
Daenen L.G., et al., "Increased Plasma Levels of Chemoresistance-inducing Fatty Acid 16:4(N-3) After Consumption of Fish and Fish Oil," JAMA Oncology, 2015, vol. 1 (3), pp. 350-358.
Durrani F., et al., "Synergistic Effect of Selenium Compounds with Radiation Therapy in Human A549 Lung Xenografts," Cancer Research, 2007, vol. 67 (9), 4 pages.
Extended European Search Report for Application No. EP17859044.4, dated Oct. 2, 2019, 10 pages.
F. Douwes, "Integrative Cancer Therapy Concept at St. George Hospital Germany".
Fahmy et al., "Protective Effects of Omega-3 Fatty Acids and/ or Nano-selenium on Cisplatin and Ionizing Radiation Induced Liver Toxicity in Rats," Indian Journal of Pharmaceutical Education and Research, 2016, vol. 50 (4), pp. 649-656.
Gandhi U.H., et al., "Selenium Suppresses Leukemia Through the Action of Endogenous Eicosanoids," Cancer Research, 2014, vol. 74 (14), pp. OF1-OF12.
International Search Report and Written Opinion for Application No. PCT/US2018/037263, dated Feb. 15, 2019, 16 pages.
International Search Report and Written Opinion for Application No. PCT/US2018/037268, dated Nov. 13, 2018, 14 pages.
Karavelioglu, Ergun "Selenium Protects Cerebral Cells by Cisplatin Induced Neurotoxicity".
Yapu, She Wen Jun. 2014, Using an animal model of mouse colon cancer stem-like cells.
Zhang, Yong Sheng, "Protective effect of selenium against cisplatin-induced nasopharyngeal cancer in male albino rats".
Yang Y.S., et al., "Enhancing Radiotherapy by Lipid Nanocapsule-mediated Delivery of Amphiphilic Gold Nanoparticles to Intracellular Membranes," ACS Nano, Sep. 2014, vol. 8 (9), pp. 8992-9002.
Zhu, et al. "Protective effect of selenium against cisplatin-induced nasopharyngeal cancer in male albino rats," Oncology Letters 12: 5068-5074, 2016. 7 pages.
Extended European Search Report dated Feb. 1, 2021, from related application 18817307.4. 6 pages.
Fakih, et al. "Selenium Protects Against Toxicity Induced by Anticancer Drugs and Augments Antitumor Activity: A Highly Selective, New, and Novel Approach for the Treatment of Solid Tumors," Clinical Colorectal Cancer, vol. 5, No. 2, 132-135. 2005. 4 pages.
Norman, et al. "The Role of Dietary Supplements during Cancer Therapy," International Research and Conference on Food, Nutrition, and Cancer. American Society for Nutritional Sciences, 2003. 6 pages.
Fernandes, et al. "Selenium compunds as therapeutic agents in cancer," Biochimica et Biophysica Acta. 2014. 19 pages.
Pardini, Ronals S. Nutiritional intervention with omega-3 fatty acids enhances tumor response to anti-neoplastic agents. ScienceDirect, Chemico-Biological Interactions, 162, 2006, 89-105. 17 pages.
Knox, Julia. "What are Cancer Stem Cells?", Very Well Health. 11 pages.
"What is Cancer?", National Cancer Institute. 8 pages.
Durrani, et al. "Synergistic effect of selenium compounds with radiation therapy in human A549 lung xenografts," Cancer Research, 2007. 4 pages.
Simone, et al. "Antioxidants and Other Nutrients Do Not Interfere With Chemotherapy or Radiation Therapy and Can Increase Kill and Increase Survival, Part 1," Alternative Therapies, Jan./Feb. 2007, vol. 13, No. 1. 15 pages.
Tallarida, Ronald J. "Drug Synergism and Dose-Effect Data Analysis," Chapman & Hall. 2000. 29 pages.
Durrani, et al. "Synergistic effect of selenium compounds with radiation therapy in human A549 lung xenografts," Cancer Research, May 2007. 4 pages.
Simone, et al. "Antioxidants and Other Nutrients Do Not Interfere With Chemotherapy or Radiation Therapy and Can Increase Kill and Increase Survival, Part 1," Alternative Therapies, Jan. 2007. 15 pages.
Tallarida, Ronald J. "Drug Synergism and Dose-Effect Data Analysis," Library of Congress. 2000. 29 pages.

* cited by examiner

COMPOSITIONS FOR ENHANCING HYPERTHERMIA THERAPY

This application is a continuation of U.S. patent application Ser. No. 17/163,419, filed Jan. 30, 2021, which is a continuation of U.S. patent application Ser. No. 16/007,524, filed Jun. 13, 2018, which claims the benefit of U.S. Provisional Application No. 62/519,090 filed on Jun. 13, 2017. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is compositions for use with hyperthermia to treat cancer.

BACKGROUND

The background description includes information that may be useful in understanding the present invention. It is not an admission that any of the information provided herein is prior art or relevant to the presently claimed invention, or that any publication specifically or implicitly referenced is prior art.

Hyperthermia (i.e., exposure to temperatures that exceed normal body temperature) has been used to treat various cancers. In some instances hyperthermia is used to cause cancer cells to become more susceptible to chemotherapeutic agents or to radiation, and serves as an adjunct to such therapies. In other instances hyperthermia can be used to kill or damage cancer cells outright, however in such applications the temperatures used risk damage to normal cells.

Hyperthermia can be applied locally, regionally, or to the whole body. Local hyperthermia is frequently used to produce very high temperatures that are restricted to a tumor site, resulting in thermal ablation. This is typically restricted to localized tumors that are exposed at the body surface or are accessible to a thin needle or probe. The size of tumors that can be treated in this fashion is also limited (generally to around two inches or less). Regional hyperthermia provides heat to a particular body region, such as a limb, organ, or body cavity. This can be accomplished by isolation perfusion (i.e., heating blood using an external device and directed it into the circulatory system supplying the region) or through the application of RF or microwave energy. The temperatures used for regional hyperthermia are too low to result in killing of cancer cells alone, so this technique is generally used as an adjunct to chemotherapy and/or radiotherapy.

In whole body hyperthermia the patient's body temperature is elevated to fever levels by application of heat (for example, using heated blankets or immersion in warm water). Temperatures as high as 107° F. are used. It is theorized that this simulates fever and provides short term activation of certain immune cells, however whole body hyperthermia is currently used as an adjunct to chemotherapy.

Attempts have been made to improve the performance of hyperthermia therapy through the use of various sensitizers. For example, U.S. Provisional Application 60/290681, to Faulk, describes conjugating sensitizing compounds (such as chemotherapeutic agents) to transferrin to produce transferring conjugates that tend to localize in cancer cells. It is not clear, however, how specific this targeting is, what degree of sensitization is achieved, or what side effects are produced by the protein conjugate drug. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Another approach is suggested in United States Patent Application Publication No. 2004/0072775, to Sobol and Gjerset. This patent application teaches genetic modification of cancer cells to re-establish the function of mutated genes (specifically, p53) that provide sensitivity to various cancer treatments, including hyperthermia. It is not clear, however, how this selective genetic modification is to be achieved in a clinical setting or to what extent it is effective in increasing sensitivity of cancer cells to hyperthermia alone.

International Patent Application Publication No. WO 2014/054884, to Cheon et al., proposes the use of magnetic nanoparticles in hyperthermia therapy. Such magnetic nanoparticles are thought to provide both a sensitizing effect and a source of heat via the application of a high frequency magnetic field. The need to localize such particles at the tumor site limits the utility of this approach. In addition, the side effects of the introduction of such magnetic nanoparticles (particularly on a repeated or long-term basis) are not clear.

U.S. patent application Publication Ser. No. 12/833,207, to Lamb et al., proposes the use of conductive "buttons" positioned at a location proximate to a tumor. The conductive buttons can be made from metals such as gold, silver, aluminum, copper, or alloys and implemented in a variety of shapes and sizes. As with Cheon et al., the need to localize the conductive buttons at the tumor site and the targeted application of heat through the conductive buttons limits the utility of this approach.

In yet another approach, U.S. Pat. No. 5,810,888 to Fenn et al., proposes the use of a thermodynamic therapy system using a radiation transmission system to focus radiation to heat a treatment area in order to activate thermosensitive drug-containing liposomes. However, this approach does not disclose the specific drugs or adjuvants delivered by the thermosensitive drug-containing liposomes.

Thus, there is still a need for a well-tolerated and/or non-toxic sensitizer that is effective in causing the death of cancer cells through the use of hyperthermia without the use of adjunct chemotherapy and/or radiotherapy.

SUMMARY OF THE INVENTION

The inventive subject matter provides compositions and methods in which selenium, fish oil, and/or selenium in combination with fish oil enhances or potentiates the effects of hyperthermia in reducing the proliferation of tumor cells. In a preferred embodiment the selenium is in the form of selenium yeast, an amino acid derived from selenium yeast, and/or a peptide derived from selenium yeast.

The inventive subject matter contemplates administering a sensitizer selected from the group consisting of selenium, fish oil, and a combination of selenium and fish oil to a cancer cell. It is contemplated that the selenium, fish oil, or a combination of selenium and fish oil are administered in sufficiently high doses depending on the application to increase the sensitivity of the target cancer cells to hyperthermia. In preferred embodiments, both selenium and fish oil are administered to advantageously increase the sensitivity of cancer cells to thermotherapy more than either fish oil or selenium alone.

One embodiment of the inventive concept is a method of treating cancer cells that includes administering fish oil formulated as listed in Table 1 and inducing hyperthermia in a patient, where the fish oil is provided in an amount that provides a synergistic effect in reducing cancer cell proliferation. In preferred embodiments, the fish oil is provided to the patient prior to the initiation of thermotherapy. In other embodiments, the fish oil can be administered concurrently with thermotherapy.

Another embodiment of the inventive concept is a method of treating cancer cells that includes administering selenium in the form of selenium yeast formulated as listed in Table 1 and inducing hyperthermia in a patient, where the selenium is provided in an amount that provides a synergistic effect in reducing cancer cell proliferation. In preferred embodiments, the selenium is provided to the patient prior to the initiation of thermotherapy. In other embodiments, the selenium can be administered concurrently with thermotherapy.

A preferred embodiment of the inventive concept is a method of treating cancer cells that includes administering both fish oil and selenium in the form of selenium yeast formulated as listed in Table 1 and inducing hyperthermia in a patient, where the fish oil and the selenium is provided in an amount that provides a synergistic effect in reducing cancer cell proliferation. In preferred embodiments, the fish oil and the selenium are provided to the patient prior to the initiation of thermotherapy. In other embodiments, the fish oil and selenium can be administered concurrently with thermotherapy.

It is contemplated that thermotherapy can be administered at any temperature that increases the temperature of bodily tissue above a normal body temperature that is effective to reduce cancer cell proliferation by allowing better perfusion of cancer cells by oxygen and medication. However, the inventive contemplates that thermotherapy can be administered at any temperature or combination of temperatures (e.g., a variable temperature hyperthermia session) between 37° C. and 44° C.

DETAILED DESCRIPTION

Figure 1:
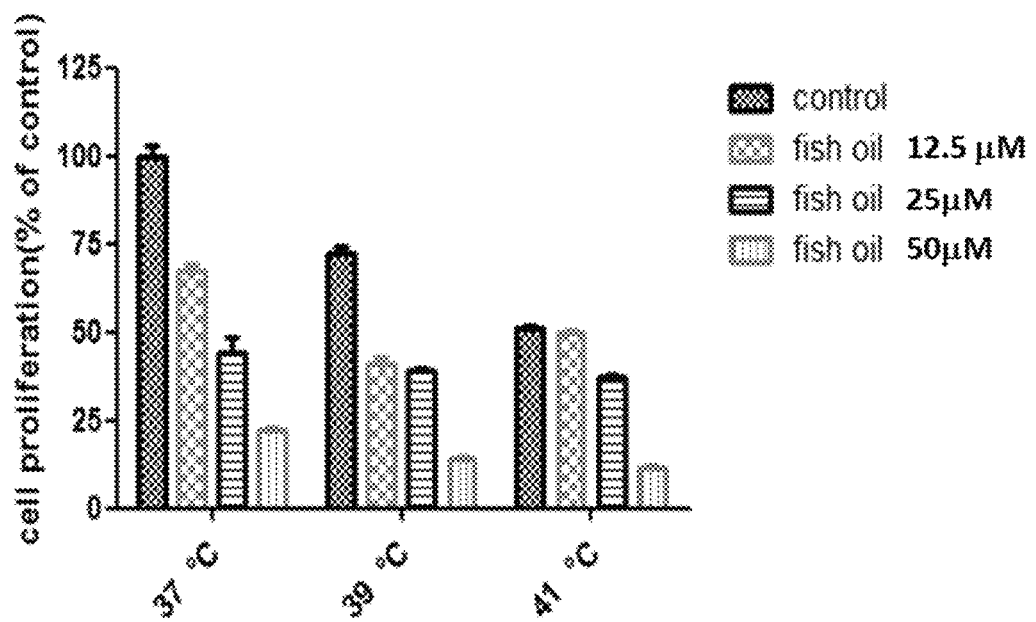
FIG. 1 is a bar graph depicting the effects of fish oil on the sensitization of MDA-MB-231 breast cancer cells to hyperthermic conditions.

Hyperthermia is commonly induced in cancer-affected tissues, such as tumors, in order to reduce, inhibit, or reverse the growth of cancer cells. Often, hyperthermia therapy accompanies radiotherapy and chemotherapy in order to maximize efficacy of anti-cancer treatments. However, conventional hyperthermia therapies do not incorporate the use of adjuvants to enhance the efficacy of hyperthermia in reducing the proliferation of cancer cells. Methods and compositions to enhance the anti-cancer effects of hyperthermia therapy using fish oil and selenium, individually or in combination, are disclosed herein. Such selenium can be in the form of selenium yeast, an amino acid derived from selenium yeast, and/or a peptide derived from selenium yeast. Approximately, as used herein, is defined as ±5% of a stated value.

As used herein, the fish oil can contain about 220 mg docosahexaenoic acid (DHA) and about 330 mg eicosapentaenoic acid (EPA), which are precursors of particular eicosanoids that can reduce inflammation in the body. In preferred embodiments, the fish oil contains between about 110 mg and about 330 mg of DHA and between about 160 mg and about 500 mg of EPA. It is contemplated that DHA and EPA combined preferably does not exceed a total of three grams administered over 24 hours. However, it is also contemplated that DHA and EPA can be present in any quantity effective to reduce the proliferation of cancer cells when used in conjunction with thermotherapy.

It is contemplated that the combination of DHA and EPA can include between about 8% and about 80% of fish oil content depending on various factors, such as the source of the omega-3 fatty acids, the processing of the oil, and the amounts of other ingredients in the oil. Sources of the fish oil include "oily" fish. For example, herring, Spanish mackerel, salmon, halibut, tuna, anchovies, and sardines can be concentrated sources of omega-3 fatty acids. However, it is also contemplated that any marine source can serve as a source of fish oil containing omega-3 fatty acids. In some embodiments fish oil can be sourced from fish with lower concentrations of omega-3 fatty acids in their tissues, including, for example, cod, flounder, and snapper. In some embodiments a fish oil equivalent that includes omega-3 fatty acids can be sourced from marine algae directly instead of from oily fish. Alternatively, fish oil equivalents including EPA and/or DHA and suitable for use in formulations of the inventive concept can be obtained from non-marine sources. For example, non-marine sources of EPA and DHA can include flaxseeds, chia seeds, hemp seeds, walnuts, and soybeans.

As used herein, it is contemplated that selenium is administered in concentrations between about 500 ng/ml and about 1500 ng/ml. Selenium salts can be toxic if administered directly. The inventive subject matter contemplates sourcing selenium from selenium yeast, which is produced by cultivating *Saccharomyces cerevisiae* or another suitable yeast in a selenium-rich media. By cultivating yeast in a selenium-rich medium, selenium can substitute for sulfur in certain amino acids (e.g. methionine, cysteine), thereby providing a nontoxic source of selenium. It is contemplated that selenium from animal sources can be in the form of selenomethionine, selenocysteine, and/or methylselenocysteine as well as proteins and peptides incorporating such amino acids.

In some embodiments, selenium can also be sourced from plants. For example, bioconcentrated selenium can be sourced from plants. In other embodiments, soluble selenium (e.g., selenate) found in soil can be a source of selenium. In yet other embodiments, selenium can be sourced from ocean water.

Surprisingly, the Inventor has found that the use of fish oil and/or selenium yeast can complement the effects of hyperthermia on cancer cells, and can do so in a synergistic (i.e. greater than additive) fashion. FIG. 1 is a bar graph depicting the effects of fish oil on the sensitization of MDA-MB-231 breast cancer ("BC") cells to hyperthermic conditions. Breast cancer ("BC") cells were subjected to control (37° C.) or hyperthermia temperatures (39° C., 41° C.). At each temperature, each set of BC cells was (1) exposed to fish oil in concentrations of 0 µM (control at 37° C.), 12.5 µM, 25 µM, and 50 µM, (2) held at 37° C., 39° C., or 41° C. for two hours, (3) held in a $CO_2$ incubator for 72 hours, and (4) checked for cell proliferation as a percentage of that of control BC cells (cells at control temperature and 0 µM fish oil concentration. The fish oil administered to the non-control concentration BC cells cultures contained 220 mg docosahexaenoic acid (DHA) and 330 mg of eicosapentaenoic acid (EPA) per gram.

BC cells held for two hours at temperatures in excess of 37° C. and administered no fish oil showed marked reductions in cell proliferations as a percentage of the control BC cell culture. At 39° C., a reduction of at least 25% in the proliferation of BC cells was observed compared to the control BC cell culture. At 41° C., a further reduction of approximately 50% in the proliferation of BC cells was observed compared to the control BC cell culture.

BC cells held for two hours at all tested temperatures and administered 12.5 µM concentrations of fish oil showed an overall reduction in the proliferation of BC cells with mixed results at varying temperatures. At 37° C., a reduction of approximately 30% was observed compared to the BC control. At 39° C., a reduction of approximately 60% was observed compared to the BC control, indicating a synergistic effect. At 41° C., a reduction of approximately 50% in the proliferation of BC cells was observed compared to the BC control.

BC cells held for two hours at all tested temperatures and administered 25 µM concentrations of fish oil showed an overall reduction in the proliferation of BC cells with mixed results at varying temperatures. At 37° C., a reduction of approximately 60% was observed compared to the control BC cell culture. At 39° C., a reduction of approximately 65% was observed compared to the control BC cell culture. At 41° C., a reduction of approximately 65% in the proliferation of BC cells was observed compared to the control BC cell culture.

BC cells held for two hours at all tested temperatures and administered 50 µM concentrations of fish oil showed an overall reduction in the proliferation of BC cells with mixed results at varying temperatures. At 37° C., a reduction of more than 75% was observed compared to the control BC cell culture. At 39° C., a reduction of approximately 80% was observed compared to the control BC cell culture. At 41° C., a reduction of approximately 85% in the proliferation of BC cells was observed compared to the control BC cell culture.

The exposure of MDA-MB-231 breast cancer cells to hyperthermia conditions (e.g. 39° C. or 41° C.) alone results in a moderate decrease in cell proliferation relative to a 37° C. control. As shown, the effects of hyperthermia are markedly enhanced (in some instances in a synergistic manner) by simultaneous exposure to fish oil in a dose-dependent manner. It should be appreciated that the temperatures utilized are within the range of temperatures that can be produced safely in a human body by conventional and relatively simple means, such as immersion in warm water and/or use of heated blankets. It should be appreciated that these temperatures are considerably below the extremes that can be employed in hyperthermia therapy.

The Applicant believes, without wishing to be bound by theory, that the effect of fish oil is reducing cell proliferation in cancer cells is due at least in part to effects particular concentrations of fish oil have when combined with elevated temperature on the cell cycle of the cancer cells.

Figure 2:
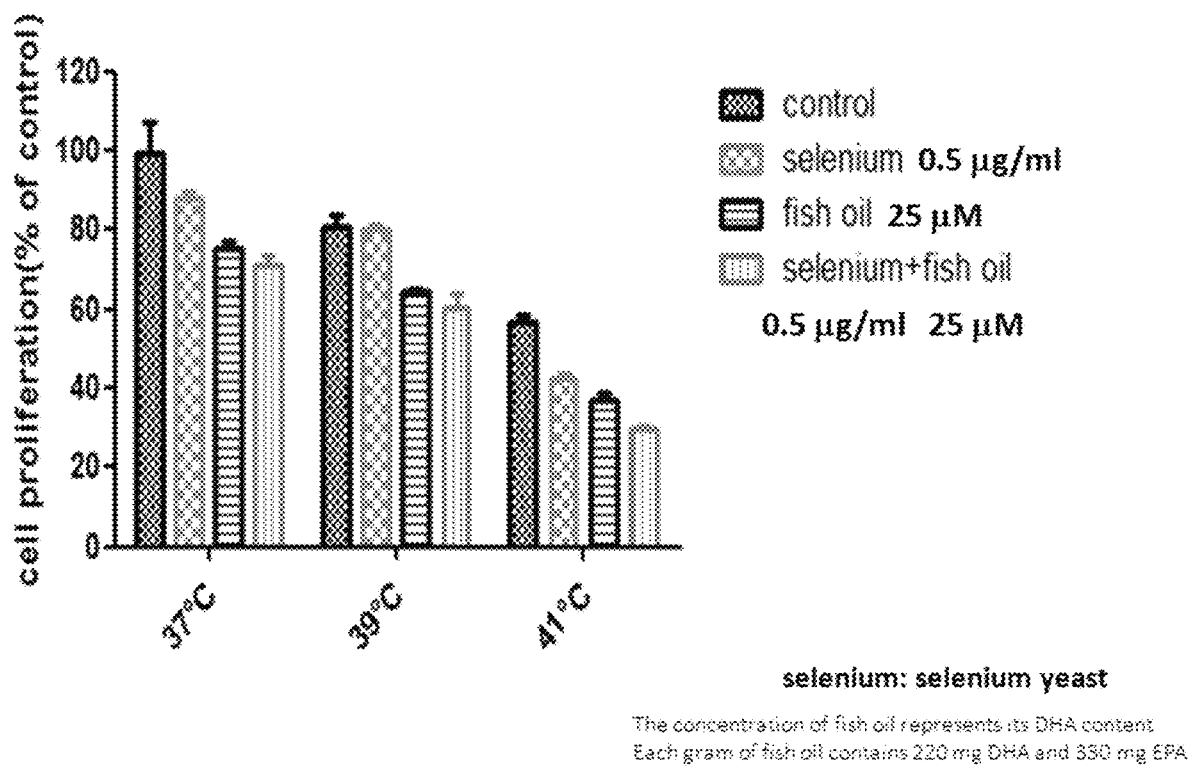
FIG. 2 is a bar graph depicting the effects of fish oil and selenium, independently and in combination, on the sensitization of HT-29 colon cancer cells to hyperthermia temperatures.

FIG. 2 is a bar graph depicting the effects of fish oil and selenium, individually and in combination, on the sensitization of HT-29 colon cancer cells ("HT cells") to hyperthermia temperatures. The sensitizing effects of selenium, fish oil, and selenium and fish oil in combination are evident in HT-29 colon cancer cells exposed to hyperthermia temperatures.

HT cells were subjected to 37° C. (control) and hyperthermia temperatures (39° C. and 41° C.). At each temperature, each set of HT cells was either (1) treated with 0.5 µg/ml of selenium, a 25 µM concentration of fish oil, or both the 0.5 µg/ml of selenium and the 25 µM concentration of fish oil, (2) held at 37° C., 39° C., or 41° C. for two hours, (3) held in a $CO_2$ incubator for 72 hours, and (4) checked for cell proliferation as a percentage of a control HT cell culture. The selenium was administered in the form of selenium yeast. It is contemplated that the source of selenium is not limited to selenium yeast and can be administered using any method known in the art. In the absence of selenium and/or fish oil, incubation at 39° C. reduced proliferation by about 20% relative to control HT cells and incubation at 41° C. reduced proliferation by about 45% relative to control HT cells.

HT cells held for two hours at all tested temperatures and treated with either 0.5 µg/ml of selenium, a 25 µM fish oil concentration, or both the 0.5 µg/ml of selenium and 25 µM fish oil showed an overall reduction in the proliferation of HT cells compared to the control HT cell culture.

At 37° C., treatment of the HT cells with 0.5 µg/ml of selenium resulted in a reduction of proliferation by approximately 10% compared to control HT cells. At 39° C., treatment of the HT cells with 0.5 µg/ml of selenium resulted in a reduction of proliferation by approximately 20% compared to the control HT cells. At 41° C., treatment of the HT cells with 0.5 µg/ml of selenium resulted in a reduction of approximately 60% compared to the control HT cell culture.

At 37° C., treatment of the HT cells with a 25 µM concentration of fish oil resulted in a reduction of proliferation by approximately 25% compared to the control HT cells. At 39° C., treatment of the HT cells with a 25 µM concentration of fish oil resulted in a reduction of proliferation by approximately 35% compared to the control HT cells. At 41° C., treatment of the HT cells with a 25 µM concentration of fish oil resulted in a reduction of proliferation by approximately 60% compared to the control HT cells.

At 37° C., treatment of the HT cells with a combination of 0.5 µg/ml of selenium and a 25 µM concentration of fish oil resulted in a reduction of proliferation by approximately 30% compared to the control HT cells. At 39° C., treatment of the HT cells with 0.5 µg/ml of selenium and a 25 µM concentration of fish oil resulted in a reduction of proliferation by approximately 35% compared to the control HT cells, indicating a synergistic effect. At 41° C., exposure to 0.5 µg/ml of selenium and a 25 µM concentration resulted in a reduction of proliferation by approximately 60% compared to the control HT cells.

The results depicted in FIG. 2 show the surprising result of reducing cell proliferation in HT cells when the cells are exposed to both fish oil and selenium. At each successive elevated temperature, the overall cell proliferation decreases. When combined with either a 0.5 μg/ml of selenium or a 25 μM concentration of fish oil, the cell proliferation decreases relative to the control, respectively. Surprisingly, the combination of both a 0.5 μg/ml of selenium and a 25 μM concentration of fish oil shows a synergistic effect by reducing cell proliferation more than either fish oil or selenium alone.

Figure 3:
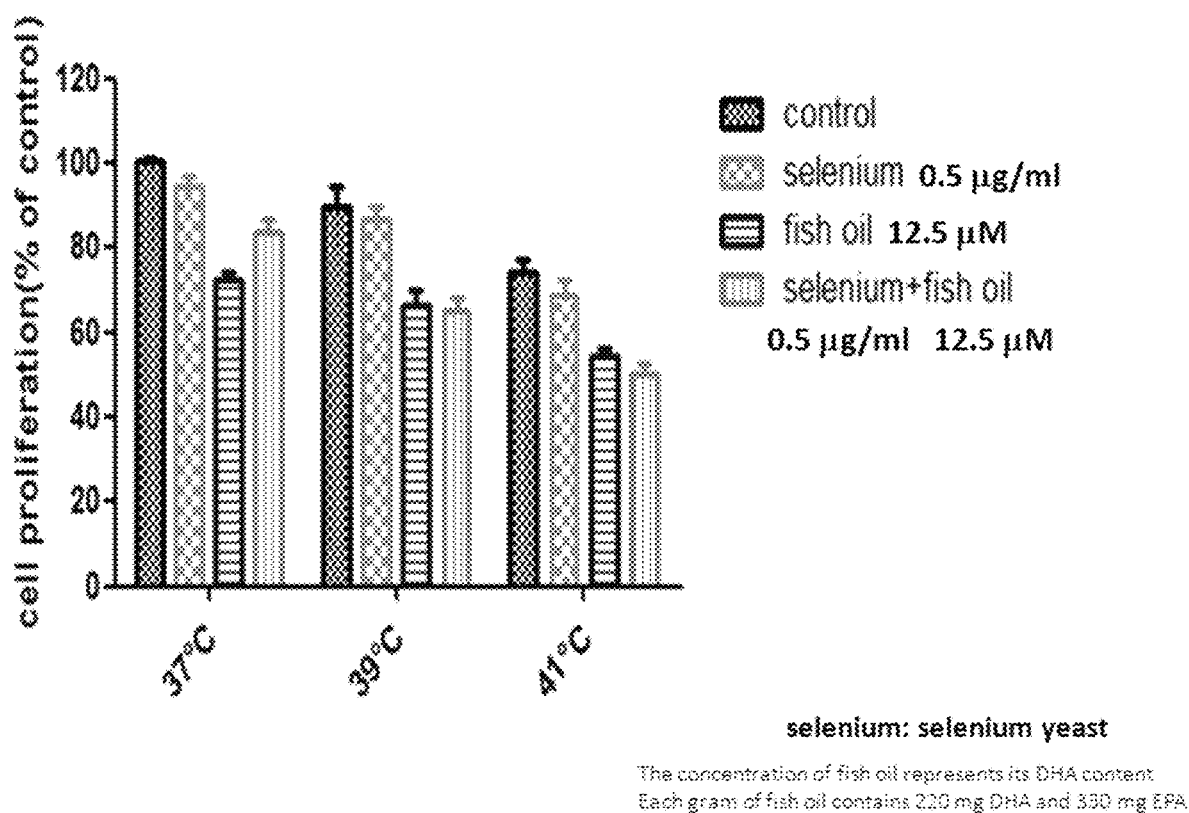
FIG. 3 is a bar graph depicting the effect of fish oil and selenium, independently and in combination, on the sensitization of BFTC-905 bladder cancer cells to hyperthermia temperatures.

FIG. 3 is a bar graph depicting the effect of fish oil and selenium, individually and in combination, on the sensitization of BFTC-905 bladder cancer cells (BFTC cells) to hyperthermia temperatures. The sensitizing effects of selenium, fish oil, and selenium and fish oil in combination are evident in BFTC cells exposed to hyperthermia temperatures.

BFTC cells were subject to control (37° C.). and hyperthermia temperatures (39° C. and 41° C.). At each temperature, each set of BFTC cells was either (1) treated with 0.5 μg/ml of selenium, a 12.5 μM concentration of fish oil, or both the 0.5 μg/ml of selenium and the 12.5 μM concentration of fish oil, (2) held at 37° C., 39° C., or 41° C. for two hours, (3) held in a $CO_2$ incubator for 72 hours, and (4) checked for cell proliferation as a percentage of the BFTC control. The selenium was administered in the form of selenium yeast. Again, it is contemplated that the source of selenium is not limited to selenium yeast and can be administered using any method known in the art.

BFTC cells held for two hours at all tested temperatures and exposed to either 0.5 μg/ml of selenium, a 12.5 μM fish oil concentration, or both the 0.5 μg/ml of selenium and the 12.5 μM concentration of fish oil showed an overall reduction in the proliferation of BFTC cells compared to the BFTC control. In the absence of selenium and/or fish oil, incubation at 39° C. reduced proliferation by about 13% relative to control BFTC cells and incubation at 41° C. reduced proliferation by about 28% relative to control BFTC cells.

At 37° C., treatment of the BFTC cells with 0.5 μg/ml of selenium resulted in a reduction of proliferation by approximately 10% compared to the BFTC control. At 39° C., treatment of the BFTC cells with 0.5 μg/ml of selenium resulted in a reduction of proliferation by approximately 15% compared to the BFTC control. At 41° C., treatment of the BFTC cells with 0.5 μg/ml of selenium resulted in a reduction of proliferation by approximately 30% compared to the BFTC control.

At 37° C., treatment of the BFTC cells with a 12.5 μM concentration of fish oil resulted in a reduction of proliferation by approximately 30% compared to the BFTC control. At 39° C., treatment of the BFTC cells with a 12.5 μM concentration of fish oil resulted in a reduction of proliferation by approximately 35% compared to the BFTC control. At 41° C., treatment of the BFTC cells with a 12.5 μM concentration of fish oil resulted in a reduction of proliferation by approximately 45% compared to the BFTC control.

At 37° C., treatment of the BFTC cells with 0.5 μg/ml of selenium and a 12.5 μM concentration of fish oil resulted in a reduction of proliferation by approximately 15% compared to the BFTC control. At 39° C., treatment of the BFTC cells with 0.5 μg/ml of selenium and a 12.5 μM concentration of fish oil resulted in a reduction of proliferation by approximately 35% compared to the BFTC control. At 41° C., exposure to 0.5 μg/ml of selenium and a 12.5 μM concentration of fish oil resulted in a reduction of proliferation by approximately 50% compared to the BFTC control.

The results depicted in FIG. 3 show the surprising result of reducing cell proliferation in BFTC cells when the cells are exposed to both fish oil and selenium. At each successive elevated temperature, the overall cell proliferation decreased. When combined with either a 0.5 μg/ml of selenium or a 25 μM concentration of fish oil, the cell proliferation decreases relative to the control, respectively. With the exception of the BFTC cell culture treated with 0.5 μg/ml of selenium and a 12.5 μM concentration of fish oil at 37° C., the mixture of selenium and fish oil shows a synergistic effect by reducing cell proliferation more than either fish oil or selenium alone.

Figure 4:
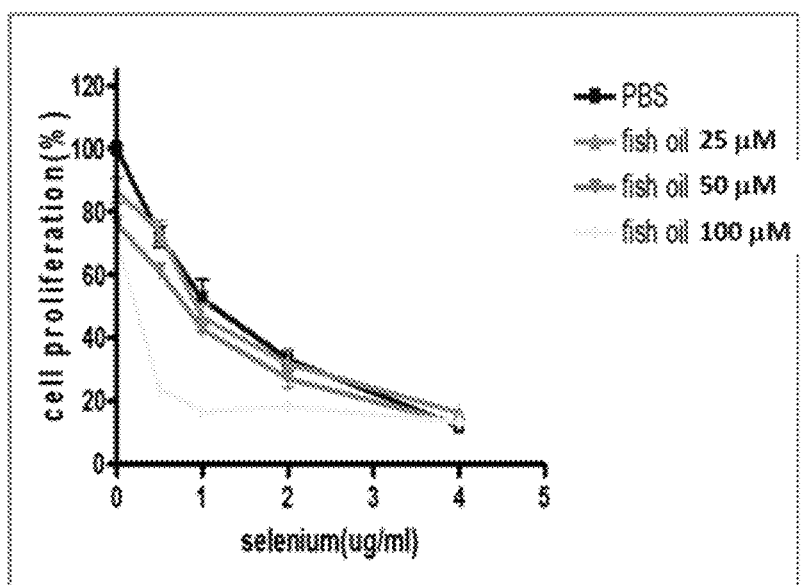
FIG. 4 is a line graph depicting the effect of selenium, fish oil, and selenium/fish oil combinations of the proliferation of A549 lung cancer cells.

FIG. 4 is a line graph depicting the effect of selenium, fish oil, and selenium/fish oil combinations of the proliferation of A549 lung cancer cells (A549 cells).

A549 cells were exposed to either 0 μM (PBS), 25 μM, 50 μM, or 100 μM fish oils. At each concentration of fish oil, each set of A5 cells was (1) exposed to either 0 μg/ml of selenium, 0.5 m/ml of selenium, 1 μg/ml of selenium, 2 μg/ml of selenium, or 4 μg/ml of selenium, (2) held at 37° C., 39° C., or 41° C. for two hours, (3) held in a $CO_2$ incubator for 72 hours, and (4) checked for cell proliferation as a percentage of PBS. The selenium was administered in the form of selenium yeast. Again, it is contemplated that the source of selenium is not limited to selenium yeast and can be administered using any method known in the art.

Each set of A549 cells held for two hours at higher concentrations of fish oil than PBS resulted in an overall reduction in the proliferation of A549 cells compared to PBS. Additionally, the treatment of cell cultures with increasing concentrations (i.e., from 0.5-4 μg/ml) of selenium shows the effects on cell proliferation relative to control (PBS only) A549 cells as selenium concentration is increased, in addition to the effects of the fish oil on the A549 cells. Synergistic effects are particularly notable at high fish oil concentrations, where the addition of even low concentrations of selenium results in a profound decrease in cell proliferation relative to that of fish oil or selenium (either individually or additively).

At 4 μg/ml of selenium, cell proliferation of each of the A549 cell cultures reduced to approximately 20% of PBS. Between 0 and 4 μg/ml of selenium, however, exposure to fish oil and selenium, each in increasing amounts, demonstrated an anti-proliferative effect with higher fish oil and selenium concentrations reducing cell proliferation more than lower fish oil and selenium concentrations.

Table 1 shows the effects of fish oil and selenium on cell cycle distribution of MDA-MB breast cancer cells (MDA-MB cells) at 39° C. and 41° C.

TABLE 1

|  | subG1 | G0/G1 | S | G2/M |
| --- | --- | --- | --- | --- |
| Control (39° C.) | 2.1% | 66.24% | 16.2% | 17.55% |
| Control (41° C.) | 4.8% | 55.91% | 22.07% | 22.01% |
| Selenium 1000 ng/ml (41° C.) | 13.9% | 59.15% | 24.36% | 16.5% |
| Fish oil 25 μM (41° C.) | 13.3% | 52.55% | 22.37% | 20.08% |
| Selenium 1000 ng/ml + Fish oil 25 μM (41° C.) | 28.94% | 56.78% | 22.13% | 21.09% |

The concentration of fish oil represents its DHA content. Each gram of fish oil contains 220 mg DHA and 330 mg EPA. Cells were incubated at hyperthermia temperatures for 2 hours and then placed in a CO2 incubator for 72 hours before a cell cycle analysis was performed. Selenium was administered in the form of selenium yeast. As shown, the use of selenium, fish oil, and selenium and fish oil in combination leads to a significant redistribution of cell cycle occupancy of these cells under hyperthermia condition. Specifically, the percentage of cells in subG1 phase (which is associated with apoptosis) is increased.

In addition to modulating cell cycle occupancy, selenium, fish oil, and selenium and fish oil in combination can modulate the concentration of certain proteins in cancer cells.

Figure 5:
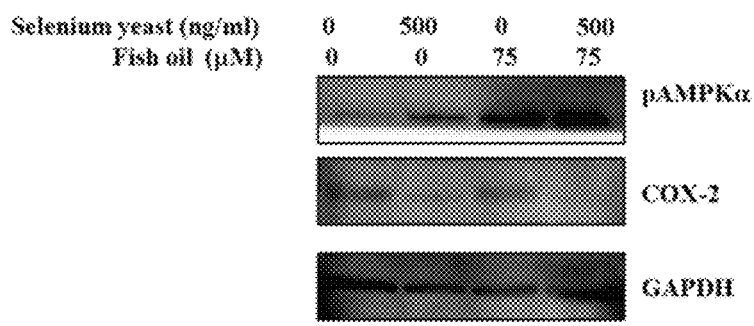
FIG. 5 depicts the modulation of pAMPKa and COX-2 concentration by selenium yeast and fish oil.

FIG. 5 depicts the modulation of pAMPKa and COX-2 concentration by selenium yeast and fish oil. Increased AMPK signaling is thought to prevent proliferation and metastasis in tumor cells. COX-2 is thought to modulate cell proliferation and apoptosis in solid tumors, with COX-2 inhibition being investigated as a therapeutic mode. Surprisingly, the Inventor found that selenium, fish oil, and selenium/fish oil combinations result in increased levels of pAMPKa and reduced levels of COX-2 in A549 lung cancer cells (GAPDH is included as a control). Such effects may contribute to the enhancement and/or synergistic effects seen when these are used in combination with hyperthermia.

Suitable formulations that incorporate fish oil and selenium yeast include the nutritional supplement formulation provided in Table 2, which incorporates fish oil and selenium yeast components along with other nutritional components. This nutritional supplement has been found to have a high level of acceptance and to have unanticipated beneficial anti-tumor activity in combination with conventional therapies. As such, the Applicant believes that use of such a nutritional supplement can provide a beneficial enhancement of the hyperthermia therapy, and can do so at lower, relatively safe temperatures that are readily achievable using conventional approaches and safer for patient use. The provision of such a safety margin in regards to body and local temperature can lead to broader acceptance and use of this non-toxic therapeutic mode.

TABLE 2

| Component | Minimum | Maximum | Unit |
|---|---|---|---|
| Maltodextrin | 10000 | 50000 | mg |
| Whey Protein Isolate | 5000 | 60000 | mg |
| Whey Protein Concentrate | 1000 | 50000 | mg |
| Fructooligosaccharides/Inulin | 40 | 15000 | mg |
| Granulated Honey | 1000 | 9000 | mg |
| Oat Fiber | 500 | 15000 | mg |
| Natural French Vanilla Flavor | 500 | 20000 | mg |
| Soy Protein | 500 | 50000 | mg |
| Brownulated Powdered Brown Sugar | 500 | 10000 | mg |
| Natural Vanilla Masking Flavor | 500 | 5000 | mg |
| Lecithin | 200 | 10000 | mg |
| Milk, Non-fat | 50 | 5000 | mg |
| Rice Protein Powder | 50 | 5000 | mg |
| Calcium Caseinate | 50 | 2000 | mg |
| Oils | | | |
| Flax Seed Oil | 100 | 7000 | mg |
| Canola Oil | 100 | 7000 | mg |
| Borage Oil | 100 | 7000 | mg |
| Olive Oil | 100 | 7000 | mg |
| Fish Oil | 150 | 10,000 | mg |
| Pure Lemon Oil | 100 | 1000 | mg |
| Pure Orange Oil | 50 | 1000 | mg |
| Mixed Tocopherols | 0.5 | 200 | mg |
| Vitamins/Minerals | | | |
| Potassium Phosphate | 200 | 1500 | mg |
| Calcium Carbonate | 100 | 5000 | mg |
| Choline Bitartrate | 150 | 2500 | mg |
| Sodium Chloride | 100 | 2000 | mg |
| Calcium Phosphate Tribasic | 100 | 2000 | mg |
| Ascorbic Acid | 50 | 3000 | mg |
| Potassium Chloride | 50 | 2000 | mg |
| Magnesium Oxide | 50 | 500 | mg |
| Selenium Yeast | 30 | 4000 | mcg |
| Chromium Yeast | 30 | 3000 | mcg |
| Molybdenum Yeast | 30 | 2000 | mcg |
| Inositol | 10 | 5000 | mg |
| Zinc Sulfate Monohydrate | 5 | 200 | mg |
| Dry Vitamin E Acetate | 5 | 2000 | IU |
| Niacinamide | 5 | 500 | mg |
| Ferric Orthophosphate | 3 | 100 | mg |
| Calcium Pantothenate | 3 | 200 | mg |
| Manganese Sulfate Monohydrate | 3 | 100 | mg |
| Beta Carotene | 1 | 100 | mg |
| Copper Gluconate | 1 | 15 | mg |
| Vitamin D3 | 25 | 5000 | IU |
| Vitamin K2 | 2 | 1000 | mcg |
| Pyridoxine HCl | 0.5 | 200 | mg |
| Potassium Iodide | 0.5 | 1500 | mg |
| Riboflavin | 0.5 | 1000 | mg |
| Thiamine Hydrochloride | 0.5 | 2500 | mg |
| Dry Vitamin K1 | 1 | 500 | mcg |
| Vitamin A Acetate | 500 | 100000 | IU |
| Folic Acid | 100 | 10000 | mcg |
| d-Biotin | 10 | 10000 | mcg |
| Vitamin B12 | 1 | 3000 | mcg |
| Amino Acids | | | |
| L-Carnitine | 300 | 30000 | mg |
| L-Glutamine | 500 | 60000 | mg |
| L-Arginine Base | 500 | 30000 | mg |
| Taurine | 50 | 2000 | mg |
| L-Lysine | 50 | 2000 | mg |
| Alpha Lipoic Acid | 10 | 1000 | mg |
| Resveratrol | 15 | 1500 | mg |
| Co-Enzyme Q10 | 10 | 5000 | mg |
| Glycine | 5 | 1000 | mg |
| Proline | 5 | 1000 | mg |
| Bacterial Cultures | | | |
| *Lact. Acidophilus* (app. 10 billion total) | 2 | 500 | mg |
| *Bifido Bifidium* (app. 10 billion total) | 2 | 500 | mg |
| *Lac. Bulgaricus* (app. 10 billion total) | 2 | 500 | mg |
| *Bifido Longum* (app. 10 billion total) | 2 | 500 | mg |
| *Strep. Thermophilus* (app. 10 billion total) | 2 | 500 | mg |
| Enzymes | | | |
| Papain | 5 | 100 | mg |
| Pepsin | 5 | 100 | mg |
| Lipase | 5 | 100 | mg |
| Bromelain | 5 | 100 | mg |
| Pancreatin 4X | 0.5 | 100 | mg |
| Lactase | 1 | 100 | mg |
| Betaine HCl | 3 | 100 | mg |
| Plant Products | | | |
| Pineapple Juice Powder | 2 | 500 | mg |
| Papaya Fruit Powder | 2 | 500 | mg |
| Quercetin | 30 | 3000 | mg |
| EGCG | 25 | 600 | mg |
| OPC | 15 | 500 | mg |
| Anthocyanins | 15 | 5000 | mg |
| Ellagic Acid | 10 | 300 | mg |
| Astaxanthin | 2 | 90 | mg |
| Fucoidan | 20 | 1500 | mg |
| Mushroom Preparation | | | |
| Cordyceps | 5 | 6000 | mg |
| Ganoderma Lucidum | 15 | 10000 | mg |
| Shiitake | 40 | 15000 | mg |
| Maitake | 30 | 15000 | mg |
| Turkey Tail | 30 | 15000 | mg |

The composition shown in Table 2 includes components that have various physiological and biochemical effects, including anti-inflammatory activity, lowering of blood glucose levels, lowering of cholesterol, and anti-tumor activity.

Other components provide supplementation of necessary vitamins, minerals, and amino acids at elevated levels. Other components (e.g. enzymes, lecithin) serve to aid in digestion and absorption of components of the composition. The combination provides a synergistic effect that exceeds the simple additive effect of individual components. It should be appreciated that the composition shown in Table 2 also includes certain flavorants (e.g. brown sugar, honey, vanilla flavor and masking agent) that serve to improve palatability and acceptance. Certain components (e.g. honey, brown sugar, milk, rice protein, casein) can provide both flavor and caloric energy. The Inventor has found that the combination of flavorants described above is effective in providing compliance with consumption of the nutritional supplement in effective amounts. In some embodiments, such flavorants can be excluded without negatively impacting the effectiveness of the nutritional supplement, thereby providing a functional nutritional supplement that includes only essential components.

It should be appreciated that components of a nutritional supplement of the inventive concept can be provided as powders, granules, liquids, suspensions, and/or emulsions. In a preferred embodiment, components of the nutritional supplement are provided as powders and/or granules. Similarly, in preferred embodiments of the inventive concepts components of the nutritional supplement are provided in relative amounts as indicated in Table 2. In some embodiments the components of the nutritional supplement are provided as a single, mixed formulation. In other embodiments components of the nutritional supplement can be provided as a kit or similar assembly containing different components of the formulation segregated or packaged separately (for example, to provide different storage conditions conducive to component stability).

Components shown in Table 2 can be provided as a single formulation (for example, as a pill, tablet, capsule, powder, liquid, suspension, etc.) or can be segregated into different formulations (for example, as pills, tablets, capsules, powders, liquids, suspensions, or combinations thereof). The amounts shown in Table 2 are exemplary, and represent typical daily dosages provided to an adult of normal stature and otherwise normal health. These amounts can be adjusted to account for differences in body mass, gender, medical condition, etc. For example, a relatively small patient weighing 40 kilos or less may receive benefit from dosages provided at or below the low end of the ranges provided, whereas a relatively large patient weighing 100 kilograms or more may require dosages provided at the high end of the ranges noted (or more). In some embodiments such a daily dose can be distributed as multiple doses throughout the day. In some of such embodiments the composition of each of such distributed doses can be identical. In other embodiments the composition of such distributed doses can be different, provided the summation of such doses provides the required supplementation.

It should be appreciated that oils found in the formulation (e.g. Flax Seed Oil, Canola Oil, Borage Oil, Olive Oil, Fish Oil, Pure Lemon Oil, Pure Orange Oil, Mixed Tocopherols) are at least consumer grade, and preferably highly purified (>95% pure). It should also be appreciated that mineral components (e.g. potassium, calcium, sodium, magnesium iron, manganese) can be provided as any safe and absorbable salt (e.g. a halide salt, phosphate salt, carbonate salt, sulfate salt), oxide, or organic complex (e.g. gluconate). It should also be appreciated that certain metals (e.g. chromium, molybdenum, selenium) are supplied in the form of a yeast component, which can include provision as a yeast-containing powder or suspension and/or as a complex with a peptide or amino acid as a result of metabolism of such metals by yeast. Similarly, it should be appreciated that preparation of various non-yeast fungi (e.g. *Cordyceps, Ganoderma Lucidum, Shiitake*, Maitake, Turkey Tail) can include powdered or granular preparation derived from dried/lyophilized fruiting bodies of such fungi.

A nutritional supplement of the inventive concept can be provided in amounts ranging from about 1 mg/kg body weight to about 100 g/kg body as a unit dose. Such a unit dose can be provided on a schedule ranging from 4 times a day to one time per week. The nutritional supplement can be provided as one or more pills or capsules. Alternatively the nutritional supplement can be provided as a powder, granular, and/or liquid formulation that is added to a food or a beverage prior to consumption. In some embodiments the nutritional supplement can be provided as a food item, such as a food or candy bar. In other embodiments the nutritional supplement can be provided as a solution, suspension, or beverage that is suitable for oral consumption and/or provision by tube feeding.

It should be appreciated that packaging that excludes light, moisture, and/or oxygen can be used to extend the shelf life of the nutritional supplement. Similarly, a nutritional supplement of the inventive concept can be packaged with a hygroscopic agent (such as silica gel), a non-reactive gas (such as $N_2$ or a noble gas), and/or under vacuum in order to extend shelf life. Such packaging can, for example, provide a nutritional supplement of the inventive concept in single unit doses and additionally provide directions for preparation and/or dosing frequency.

The present invention contemplates using hyperthermia in conjunction with nutritional supplements with varying concentrations of fish oil and selenium. Hyperthermia regimes consist of heating body tissue to supra-normal body temperatures to sensitize cancer cells to treatment methods or to directly kill cancer cells. For example, hyperthermia regimes can be administered for 45-60 minutes over 4-12 sessions. Hyperthermia can be applied locally, regionally, or to the whole body and sourced from microwave energy, radiofrequency energy, ultrasound energy, or any other source of energy sufficient to heat tissue to supra-normal temperatures. In some embodiment, heat can be directly applied to the cancerous tissue, including, for example, by inserting a heated probe inside a tumor.

In one embodiment, a nutritional supplement containing a 25 μM concentration of fish oil is administered to a patient to be ingested orally. After waiting a sufficient amount of time to allow the fish oil to be absorbed into the blood stream (e.g., over a period of two hours), heat is applied to the cancerous tissue to raise the temperature of the tissue to supra-normal levels for a 45 minute duration. For example, a microwave heating element can be applied locally to the surface of the skin of the patient above a tumor. In another example, a probe can be inserted into a tumor and heated. In yet another example, a patient can be instructed to wear a whole body suit and the patient's body can be heated to 39° C.

In another embodiment, a nutritional supplement containing 1000 ng/ml of selenium in the form of selenium yeast can be administered to a patient to be ingested orally. After waiting a sufficient amount of time to allow the selenium to be absorbed into the blood stream (e.g., over a period of two hours), heat is applied to the cancerous tissue to raise the temperature of the tissue to supra-normal levels for a 60 minute duration. As in the preceding embodiment, a microwave heating element can be applied locally to the surface of the skin of the patient above a tumor. In another example, a probe can be inserted into a tumor and heated. In yet another example, a patient can be instructed to wear a whole body suit and the patient's body can be heated to 39° C.

In a preferred embodiment, a nutritional supplement containing a 25 µM concentration of fish oil and 1000 ng/ml of selenium in the form of selenium yeast can be administered to a patient to be ingested orally. After waiting a sufficient amount of time to allow the fish oil and the selenium to be absorbed into the blood stream (e.g., over a period of two hours), heat is applied to the cancerous tissue to raise the temperature of the tissue to supra-normal levels for a 55 minute duration. As in the preceding embodiment, a microwave heating element can be applied locally to the surface of the skin of the patient above a tumor. In another example, a probe can be inserted into a tumor and heated. In yet another example, a patient can be instructed to wear a whole body suit and the patient's body can be heated to 39° C.

It is contemplated that the fish oil and selenium individually or in combination and in any respective concentrations can be administered using any method effective to expose the cancer cells to the fish oil and/or the selenium. For example, fish oil and selenium can be directly injected into the cancerous tissue. In another example, fish oil and selenium can be applied topically to the skin or to the outer most tissue of an organ to be absorbed into cancerous tissue.

It is also contemplated that heat can be applied to the cancerous tissue using any method known in the art. For example, a heated element can be directly applied to the cancerous tissue or tissue surrounding the cancerous tissue to transfer heat through conduction. In another example, a heating element giving of electromagnetic energy waves can be used to transfer heat including, for example, an infrared heating element.

One should appreciate that the disclosed techniques provide many advantageous technical effects including sensitizing tumor cells to the effects of hyperthermia using well-tolerated substances and without the use of radiation and/or chemotherapeutic agents.

The description of the inventive subject matter herein includes information that may be useful in understanding the present invention. It is not an admission that any of the information provided herein is prior art or relevant to the presently claimed invention, or that any publication specifically or implicitly referenced is prior art.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The detailed description provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A nutritional supplement for decreasing proliferation of a cancer cell being treated with a hyperthermia therapy protocol, comprising:
    an effective first amount of fish oil; and
    an effective second amount of selenium, wherein selenium is provided as selenium yeast,
    wherein the effective first amount of fish oil and the effective second amount of selenium provide a combined synergistic effect in decreasing proliferation of the cancer cell being treated with the hyperthermia therapy protocol that is greater than a summation of effects of the first effective amount of fish oil and the second effective amount of selenium when provided as monotherapies with the hyperthermia therapy protocol, or wherein
    the first effective amount of fish oil provides 12.5 µM to 25 µM fish oil to the cancer cell, the second effective amount of selenium provides 0.5 µg/mL selenium to the cancer cell, and the hyperthermia therapy protocol comprises a temperature of 39° C. to 41° C.

2. The nutritional supplement of claim 1, where in the nutritional supplement comprises at least three components selected from the group consisting of 10,000 to 50,000 mg maltodextrin; 5,000 to 60,000 mg whey protein isolate; 1,000 to 50,000 mg whey protein concentrate; 40 to 15,000 mg fructooligosaccharides/inulin; 1,000 to 9,000 mg granulated honey; 500 to 15,000 mg oat fiber; 500 to 20,000 mg natural French Vanilla flavor; 500 to 50,000 mg soy protein; 500 to 10,000 mg brownulated powdered brown sugar; 500 to 5,000 mg natural vanilla masking flavor; 200 to 10,000 mg lecithin; 50 to 5,000 mg non-fat milk; 50 to 5,000 mg rice protein powder; 50 to 2,000 mg calcium caseinate; 100 to 7,000 mg flax seed oil; 100 to 7,000 mg canola oil; 100 to 7,000 mg borage oil; 10 to 7,000 mg olive oil; 150 to 10,000 mg fish Oil; 100 to 1,000 mg pure lemon oil; 50 to 1,000 mg pure orange oil; 0.5 to 200 mg mixed tocopherols; 200 to 1,500 mg potassium phosphate; 100 to 5,000 mg calcium carbonate; 150 to 2,500 mg choline bitartrate; 100 to 2,000 mg sodium chloride; 100 to 2,000 mg calcium phosphate tribasic; 50 to 3,000 mg ascorbic acid; 50 to 2,000 mg potassium chloride; 50 to 500 mg magnesium oxide; 30 to 4,000 mcg selenium yeast; 30 to 3,000 mcg chromium yeast; 30 to 2,000 mcg molybdenum yeast; 10 to 5,000 mg inositol; 5 to 200 mg zinc sulfate monohydrate; 5 to 2,000 IU dry vitamin E acetate; 5 to 500 mg niacinamide; 3 to 100 mg ferric orthophosphate; 3 to 200 mg calcium pantothenate; 3 to 100 mg manganese sulfate monohydrate; 1 to 100 mg beta carotene; 1 to 15 mg copper gluconate; 25 to 5,000 IU vitamin D3; 2 to 1000 mcg vitamin K2; 0.5 to 200 mg pyridoxine HCl; 0.5 to 1,500 mg potassium iodide; 0.5 to 1,000 mg riboflavin; 0.5 to 2,500 mg thiamine hydrochloride; 1 to 500 mcg dry vitamin K1; 500 to 100,000 IU vitamin A acetate; 100 to 10,000 mcg folic acid; 10 to 10,000 mcg d-biotin; 1 to 3,000 mcg vitamin B12; 300 to 30,000 mg L-carnitine; 500 to 60,000 mg L-glutamine; 500 to 30,000 mg L-arginine base; 50 to 2,000 mg taurine; 50 to 2,000 mg L-lysine; 10 to 1,000 mg alpha lipoic acid; 15 to 1,500 mg resveratrol; 10 to 5,000 mg co-enzyme Q10; 5 to 1,000 mg glycine; 5 to 1,000 mg proline; 2 to 500 mg *Lactobacillus acidophilus;* 2 to 500 mg *Bifidobacterium* bifidium; 2 to 500 mg *Lactobacillus bulgaricus;* 2 to 500 mg *Bifidobacterium longum;* 2 to 500 mg *Streptococcus thermophilus;* 5 to 100 mg papain; 5 to 100 mg pepsin; 5 to 100 mg lipase; 5 to 100 mg bromelain; 1 to 100 mg lactase; 3 to 100 mg betaine HCl; 2 to 500 mg pineapple juice powder; 2 to 500 mg *papaya* fruit powder; 30 to 3,000 mg quercetin; 25 to 600 mg epigallocatechin gallate (EGCG); 15 to 500 mg oligomeric proanthocyanidin (OPC); 15 to 5,000 mg anthocyanins; 10 to 300 mg ellagic acid; 2 to 90 mg astaxanthin; 20 to 1,500 mg fucoidan; 5 to 6,000 mg *Cordyceps;* 15 to 10,000 mg *Ganoderma lucidum;* 40 to 15,000 mg *Shiitake;* 30 to 15,000 mg Maitake; and 30 to 15000 mg Turkey Tail.

3. The nutritional supplement of claim 1, where in the nutritional supplement comprises at least three components selected from the group consisting of 10,000 to 50,000 mg maltodextrin; 5,000 to 60,000 mg whey protein isolate; 1,000 to 50,000 mg whey protein concentrate; 40 to 15,000 mg fructooligosaccharides/inulin; 1,000 to 9,000 mg granulated honey; 500 to 15,000 mg oat fiber; 500 to 20,000 mg natural French Vanilla flavor; 500 to 50,000 mg soy protein; 500 to 10,000 mg brownulated powdered brown sugar; 500 to 5,000 mg natural vanilla masking flavor; 200 to 10,000 mg lecithin; 50 to 5,000 mg non-fat milk; 50 to 5,000 mg rice protein powder; 50 to 2,000 mg calcium caseinate; 100 to 7,000 mg flax seed oil; 100 to 7,000 mg canola oil; 100 to 7,000 mg borage oil; 10 to 7,000 mg olive oil; 150 to 10,000 mg fish Oil; 100 to 1,000 mg pure lemon oil; 50 to 1,000 mg pure orange oil; 0.5 to 200 mg mixed tocopherols; 200 to 1,500 mg potassium phosphate; 100 to 5,000 mg calcium carbonate; 150 to 2,500 mg choline bitartrate; 100 to 2,000 mg sodium chloride; 100 to 2,000 mg calcium phosphate tribasic; 50 to 3,000 mg ascorbic acid; 50 to 2,000 mg potassium chloride; 50 to 500 mg magnesium oxide; 30 to 4,000 mcg selenium yeast; 30 to 3,000 mcg chromium yeast; 30 to 2,000 mcg molybdenum yeast; 10 to 5,000 mg inositol; 5 to 200 mg zinc sulfate monohydrate; 5 to 2,000 IU dry vitamin E acetate; 5 to 500 mg niacinamide; 3 to 100 mg ferric orthophosphate; 3 to 200 mg calcium pantothenate; 3 to 100 mg manganese sulfate monohydrate; 1 to 100 mg beta carotene; 1 to 15 mg copper gluconate; 25 to 5,000 IU vitamin D3; 2 to 1000 mcg vitamin K2; 0.5 to 200 mg pyridoxine HCl; 0.5 to 1,500 mg potassium iodide; 0.5 to 1,000 mg riboflavin; 0.5 to 2,500 mg thiamine hydrochloride; 1 to 500 mcg dry vitamin K1; 500 to 100,000 IU vitamin A acetate; 100 to 10,000 mcg folic acid; 10 to 10,000 mcg d-biotin; 1 to 3,000 mcg vitamin B12; 300 to 30,000 mg L-carnitine; 500 to 60,000 mg L-glutamine; 500 to 30,000 mg L-arginine base; 50 to 2,000 mg taurine; 50 to 2,000 mg L-lysine; 10 to 1,000 mg alpha lipoic acid; 15 to 1,500 mg resveratrol; 10 to 5,000 mg co-enzyme Q10; 5 to 1,000 mg glycine; 5 to 1,000 mg proline; 2 to 500 mg *Lactobacillus acidophilus;* 2 to 500 mg *Bifidobacterium* bifidium; 2 to 500 mg *Lactobacillus bulgaricus;* 2 to 500 mg *Bifidobacterium longum;* 2 to 500 mg *Streptococcus thermophilus;* 5 to 100 mg papain; 5 to 100 mg pepsin; 5 to 100 mg lipase; 5 to 100 mg bromelain; 1 to 100 mg lactase; 3 to 100 mg betaine HCl; 2 to 500 mg pineapple juice powder; 2 to 500 mg *papaya* fruit powder; 30 to 3,000 mg quercetin; 25 to 600 mg epigallocatechin gallate (EGCG); 15 to 500 mg oligomeric proanthocyanidin (OPC); 15 to 5,000 mg anthocyanins; 10 to 300 mg ellagic acid; 2 to 90 mg astaxanthin; 20 to 1,500 mg fucoidan; 5 to 6,000 mg *Cordyceps;* 15 to 10,000 mg *Ganoderma lucidum;* 40 to 15,000 mg *Shiitake;* 30 to 15,000 mg Maitake; and 30 to 15000 mg Turkey Tail.

\* \* \* \* \*